(12) United States Patent
Abbott et al.

(10) Patent No.: US 6,589,216 B1
(45) Date of Patent: Jul. 8, 2003

(54) VAGINAL DOUCHES, VAGINAL DOUCHE APPLICATORS AND METHODS OF VAGINAL DOUCHING

(75) Inventors: Chun Lim Abbott, Pittsburgh, PA (US); Dominic C. Abbott, Pittsburgh, PA (US); John L. Moss, Monroeville, PA (US)

(73) Assignee: Abbott Research Group, Inc., Pittsburgh, PA (US)

( * ) Notice: Subject to any disclaimer, the term of this patent is extended or adjusted under 35 U.S.C. 154(b) by 0 days.

(21) Appl. No.: 10/077,256

(22) Filed: Feb. 20, 2002

(51) Int. Cl.7 .............................................. A61M 31/00
(52) U.S. Cl. ........................ 604/279; 604/257; 604/259; 604/515
(58) Field of Search .................... 604/279, 39, 212, 604/257, 259, 515

(56) References Cited

U.S. PATENT DOCUMENTS 1,098,220 A * 5/1914 Borsody ..................... 604/279
1,338,464 A * 4/1920 Shafer ........................ 604/279
6,190,365 B1 * 2/2001 Abbott et al. ............... 604/279

* cited by examiner

Primary Examiner—Brian L. Casler
Assistant Examiner—Lina R Kontos

(57) ABSTRACT

A vaginal douche comprises a vaginal douche applicator for introduction in the vaginal canal and a source or supply of douching fluid connected with the vaginal douche applicator. The vaginal douche applicator comprises an applicator body, a head joined to the applicator body and an internal passage for being supplied with douching fluid. Rearward discharge holes and forward discharge holes in the head communicate with the passage and discharge douching fluid into the vaginal canal. The rearward discharge holes face proximally toward the applicator body, and the forward discharge holes face distally and outwardly from the head at an angle. Douching fluid discharged into the vaginal canal is directed proximally along a plurality of external head channels of the head toward a plurality of external body channels of the applicator body. Douching fluid is directed proximally along the body channels toward the vaginal opening for exit from the vaginal canal. The vaginal douche and vaginal douche applicator are used in a method of vaginal douching.

52 Claims, 7 Drawing Sheets

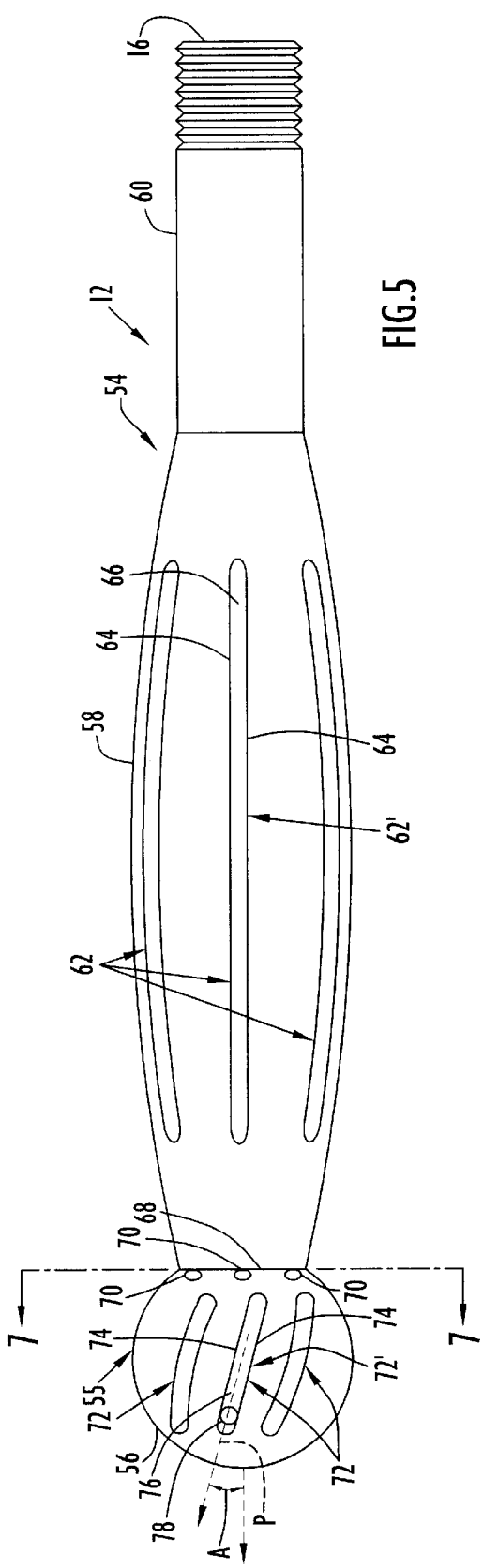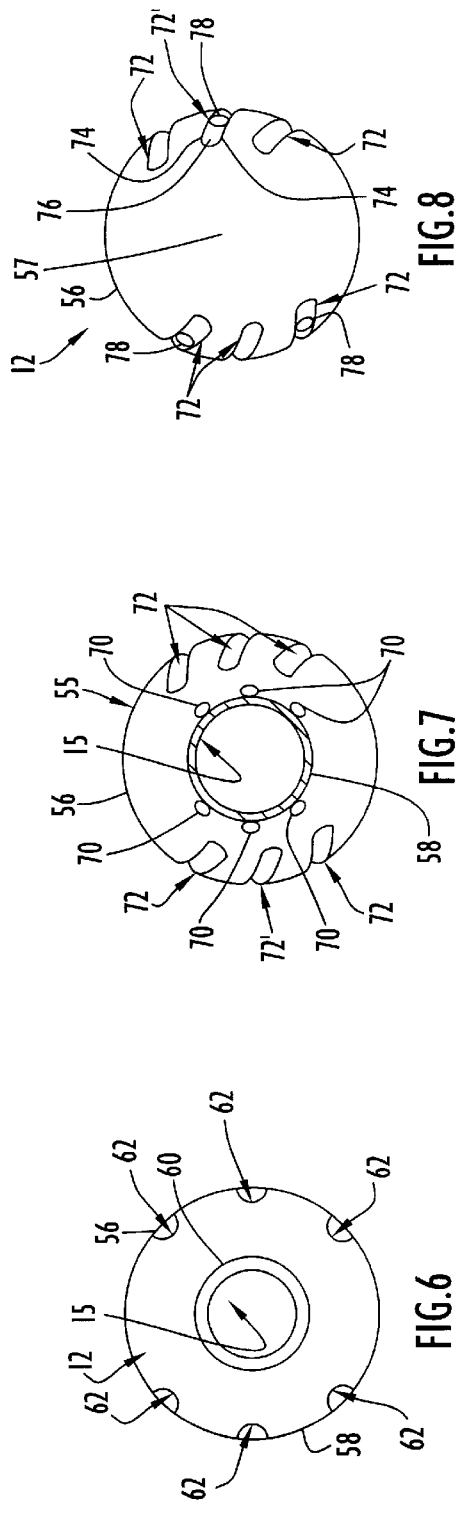

VAGINAL DOUCHES, VAGINAL DOUCHE APPLICATORS AND METHODS OF VAGINAL DOUCHING

BACKGROUND OF THE INVENTION

1. Field of the Invention

The present invention relates generally to vaginal douches and, more particularly, to vaginal douches and vaginal douche applicators for neutralizing vaginal odors by contact of vaginal tissue with a stainless steel surface of the applicators and to methods of vaginal douching.

2. Brief Discussion of the Related Art

In the area of female personal hygiene and gynecological health, vaginal douches have been proposed for reducing vaginal odors. Conventional vaginal douches typically involve the application of a stream of douching fluid through a vaginal douche applicator and into the vaginal canal of the user. Water alone as a douching fluid is not effective at significantly alleviating vaginal odors or the sources of vaginal odors, such as bacteria, when used in conjunction with vaginal douche applicators that do not have a stainless steel external surface. Since it is most typical for vaginal douche applicators to be made of inexpensive disposable materials, such as plastic, conventional vaginal douches usually include various commercial douching agents or substances, such as cleansing and/or disinfecting agents and/or perfumes, to be mixed with water by the user to obtain a douching fluid or supplied to the user as a prepared douching fluid. However, commercial douching agents or substances tend not to be effective in alleviating some vaginal odors or may serve merely to temporarily mask vaginal odors. Even when commercial douching agents or substances are effective in alleviating vaginal odors, the vaginal odors may return shortly after douching.

Another problem associated with conventional vaginal douches is that the douching agents or substances may cause irritation in some users and/or tend to alter the normal pH (acid/ alkaline) or chemical balance of the vaginal canal. When the vaginal canal becomes irritated and/or has its normal pH (acid/alkaline) or chemical balance disturbed or altered, an increased risk is presented for vaginitis, including yeast, bacterial vaginosis and other infections. Vinegar has been proposed as a natural douching agent or substance which, when mixed with water in the proper proportion, presents a douching fluid that closely mimics the normal pH of the vaginal canal. However, douching fluids consisting of vinegar and water tend not to be effective against vaginal odors for any meaningful length of time.

A further problem associated with conventional vaginal douches is that many vaginal douche applicators discharge douching fluid directly at and/or toward the cervix with sufficient force or pressure so that douching fluid may enter the cervical canal. When this occurs, vaginal debris such as bacteria and other harmful or undesirable organisms carried by the douching fluid may pass through the cervix and enter the uterine cavity, potentially causing pelvic inflammatory disease. Where douching fluid is not discharged toward the cervix and the upper portion of the vaginal canal, however, odors will not be eliminated or will quickly return since the cervix as well as the vaginal tissue produce odoriferous secretions. Hence, failure to wash off the cervix and the upper portion, or fornix, of the vaginal canal will yield an incomplete douching. An additional problem of conventional vaginal douches relates to the inadequacy of the vaginal douche applicators in maintaining an unobstructed gravity flow of douching fluid from the vaginal canal. Since the vaginal canal is normally collapsed or contracted, it has a tendency to clamp down on a vaginal douche applicator inserted therein. Accordingly, douching fluid containing vaginal debris may be prevented from exiting the vaginal canal and may collect and become trapped in the vaginal upper canal thereby allowing bacteria and other harmful organisms, including those responsible for sexually transmitted diseases, to remain in and move higher in the vaginal canal after douching. During douching, trapped douching fluid may build up in the vaginal canal with a sufficient pressure head that the douching fluid is detrimentally forced into and/or through the cervical canal. Conventional vaginal douches are also problematic for their failure to limit, regulate or control the flow of douching fluid into the vaginal douche applicators such that the douching fluid is discharged from the applicators at pressures high enough to force the douching fluid into the cervix. Other drawbacks to conventional vaginal douches are that the vaginal douche applicators are not designed for reuse and are actually unsuitable for reuse due to the difficulties involved in maintaining cleanliness for repeated use.

Although conventional vaginal douches may undesirably alter normal vaginal environments, douching has been found to benefit vaginal environments that are already undesirably altered or disturbed. Normal, balanced vaginal environments are characterized by trace numbers of yeast cells, trace numbers of coccoid bacteria called Gardnerella vaginalis and a preponderance of lactobacillus bacteria. Vaginal environments that are disturbed or unbalanced include those having an overgrowth of coccoid bacteria. Coccoid overgrowth is associated with bacterial vaginosis, characterized by an unpleasant odor and a change in consistency of vaginal secretions which adversely impact personal comfort and confidence. Inflamation associated with bacterial vaginosis may extend to the fallopian tubes and endometrium. Also, the production of amines, such as putrescine and cadaverine, by the coccoid bacteria may have carcinogenic effects, with there being a statistical association between coccoid overabundance and cervicitis and epithelial changes. The effects of bacterial vaginosis are believed to synergize with human immunodeficiency virus (HIV) and human papilloma virus (HPV). In the case of HIV, the presence of bacterial vaginosis may cause increased numbers of virus secreting cells and/or may enhance cell binding by the virus, thereby resulting in an increased risk for HIV transmission. In the case of HPV, the presence of bacterial vaginosis may result in the survival of oncogenic cell mutations related to cervical carcinoma. An excess of yeast cells may lead to problems, one such problem being fungal proliferation or yeast infections.

A relationship has been established between bacterial vaginosis and recent coitus. Since semen is alkaline, the normal pH of the vaginal canal increases significantly after coitus and changes from mildly acidic to alkaline such that the normal pH (acid/alkaline) of the vaginal environment is unbalanced or disturbed. This higher pH promotes a rapid increase in coccoid production and may result in coccoid overgrowth leading to bacterial vaginosis and its various adverse consequences. Accordingly, post-coital vaginal douching to wash away semen and/or coccoid bacteria may prevent bacterial vaginosis and/or counteract already existing bacterial vaginosis. However, because of the various problems associated with conventional vaginal douches, vaginal douching has not been widely adopted and used, particularly in the United States, as a preventative and/or treatment for bacterial vaginosis.

Elimination of vaginal odors by contacting vaginal tissue with a stainless steel surface of a vaginal douche applicator in the presence of water is proposed in U.S. Pat. No. 6,190,365 B1 to Abbott et al, the entire disclosure of which is incorporated herein by reference. The vaginal douche applicators and methods of vaginal deodorization disclosed by Abbott et al are effective in eliminating vaginal odors but can be rendered more effective at odor elimination by further maximizing contact between the vaginal tissue and the stainless steel surface of the vaginal douche applicator. Moreover, it would be desirable to further enhance the safety and efficacy of the applicators and methods disclosed by Abbott et al to increase medical and public acceptance of vaginal douching and, in particular, adoption of vaginal douching as a preventative and/or treatment for unbalanced vaginal environments.

SUMMARY OF THE INVENTION

Accordingly, it is a primary object of the present invention to overcome the aforementioned disadvantages of prior vaginal douches.

Another object of the present invention is to enhance the safety and efficacy of vaginal douches.

A further object of the present invention is to maximize contact of vaginal tissue with a stainless steel surface of a vaginal douche applicator.

An additional object of the present invention is to minimize alteration of normal vaginal environments as a result of vaginal douching.

Furthermore, it is an object of the present invention to minimize alterations in vaginal pH as a result of vaginal douching.

It is also an object of the present invention to break the chemical bonds of odoriferous compounds responsible for vaginal odors.

The present invention has as another object to create a controlled sheeting effect of douching fluid flow over a surface of a vaginal douche applicator.

A still further object of the present invention is to maintain a cleansing or rinsing flow of douching fluid out of the vaginal canal during vaginal douching.

Moreover, it is an object of the present invention to control the direction and force of douching fluid flow toward the cervix during vaginal douching.

Yet another object of the present invention is to prevent the accumulation of douching fluid in the vaginal canal during vaginal douching.

The present invention has as a further object to prevent the build-up of an undesirably high pressure head from douching fluid in the vaginal canal during vaginal douching.

Additionally, it is an object of the present invention to control the flow of douching fluid into a vaginal douche applicator to avoid discharging the douching fluid from the vaginal douche applicator into the vaginal canal at undesirably high pressures.

Still another object of the present invention is to achieve low pressure directional washing of the cervix and vaginal fornix with douching fluid during vaginal douching.

An additional object of the present invention is to produce a self-cleaning effect during insertion of a vaginal douche applicator into the vaginal canal to avoid transferring harmful organisms from the lower portion to the upper portion of the vaginal canal.

A still further object of the present invention is to promote medically safe reuse of a vaginal douche applicator.

The present invention has as an additional object to utilize vaginal douching as a preventative or a treatment for bacterial vaginosis.

It is also an object of the present invention to normalize disturbed vaginal environments by vaginal douching.

Some of the advantages of the present invention are that the reaction of the stainless steel surfaces of the vaginal douche applicators with odor-linked chemical bonds is maximized; the cervical os is not directly impacted with douching fluid; the vaginal douche applicators can illicit an antimicrobial reaction; effective deodorization of the vaginal canal may be achieved using only water as the douching fluid; the douching fluid may include treatment substances or additives, such as pH lowering, pH increasing, antibiotic, antiseptic, probiotic and/or microbicide substances or additives to obtain various effects or reactions; treatment substances or additives may be applied to the vaginal canal separately from douching using the vaginal douche applicators to apply the treatment substances or additives; the vaginal douche applicators provide a smearing or spreading effect such that treatment substances or additives may be more widely and more uniformly disbursed in the vaginal canal; desquamated cells, debris, bacteria and other harmful or undesirable organisms are flushed out of the vaginal canal; a "leaky" or imperfect seal is maintained between the vaginal douche applicators and the wall of the vaginal canal no matter how tightly the vaginal wall contracts around or clamps down on the vaginal douche applicators; the vaginal douche applicators are innately less expensive since they are reusable; post-coital douching is promoted since the vaginal douche applicators can be used repeatedly on demand; and the vaginal douche applicators may be provided with specialized coatings or finishes to obtain various reactions or effects.

These and other objects, advantages and benefits are realized with the present invention as generally characterized in a vaginal douche comprising a vaginal douche applicator for introduction in the vaginal canal and a source or supply of douching fluid connected with the vaginal douche applicator. The vaginal douche applicator comprises an applicator body, a head joined to the applicator body and an internal passage extending through the applicator body and terminating within the head. The applicator body comprises an open rearward end in communication with the passage, a forward end joined to the head and a plurality of external body channels along an external surface of the applicator body. The open rearward end is connectable with the source or supply of douching fluid, whereby douching fluid is supplied to the passage. The head comprises a plurality of rearward discharge holes in communication with the passage, a plurality of forward discharge holes in communication with the passage and a plurality of external head channels along an external surface of the head. The rearward discharge holes face proximally or rearwardly toward the applicator body such that douching fluid discharged therefrom is directed to flow along the interface between the applicator body and the vaginal wall. The forward discharge holes, which are spaced distally or forwardly from the rearward discharge holes, face distally or forwardly and face outwardly from the head at an angle so that douching fluid discharged therefrom is directed to flow toward the sides of the cervix. The head channels extend along the head in a direction transverse to a central longitudinal axis of the vaginal douche applicator, and the head channels direct discharged douching fluid toward the body channels. The body channels extend along the applicator body in the same direction as the central longitudinal axis of the vaginal douche applicator, and the body channels direct discharged douching fluid toward the vaginal opening for exit from the vaginal canal. In a particularly preferred vaginal douche applicator, the forward discharge holes face outwardly from the head at an angle of 30° to the central longitudinal axis of the vaginal douche applicator; the head channels are disposed at an angle of 30° to the central longitudinal axis of the vaginal douche applicator, with each forward discharge hole disposed in a respective one of the head channels; and the applicator body comprises a segment having an external cross-sectional configuration that tapers toward the forward and rearward ends of the applicator body. In a particularly preferred vaginal douche, the vaginal douche applicator has a stainless steel external surface and the douching fluid comprises water to effect neutralization of vaginal odors due to contact of the stainless steel with the vaginal tissue in the presence of water.

A method of vaginal douching according to the present invention is generally characterized in the steps of introducing a vaginal douche applicator through the vaginal opening into the vaginal canal, supplying douching fluid to an internal passage of the vaginal douche applicator, discharging the douching fluid into the vaginal canal through forward discharge holes in a head of the vaginal douche applicator such that the douching fluid is directed to flow toward the sides of the cervix, discharging the douching fluid into the vaginal canal through rearward discharge holes in the head such that the douching fluid is directed to flow over a body of the vaginal douche applicator in the direction of the vaginal opening, directing discharged douching fluid along external head channels of the head such that discharged douching fluid is directed toward external body channels of the body, directing discharged douching fluid along the body channels in the direction of the vaginal opening such that discharged douching fluid exits the vaginal canal, and withdrawing the vaginal douche applicator from the vaginal canal. In a method of vaginal deodorization, a vaginal douche applicator having a stainless steel external surface is introduced in the vaginal canal, the douching fluid comprises water and vaginal odors are neutralized due to contact of vaginal tissue with the stainless steel external surface in the presence of the water.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 5 is a side view of a vaginal douche applicator according to the present invention.

FIG. 6 is a proximal end view of the vaginal douche applicator.

FIG. 7 is a sectional view of the vaginal douche applicator taken along line 7—7 in FIG. 5.

FIG. 8 is a distal end view of the vaginal douche applicator.

DESCRIPTION OF THE PREFERRED EMBODIMENTS

Figure 1:
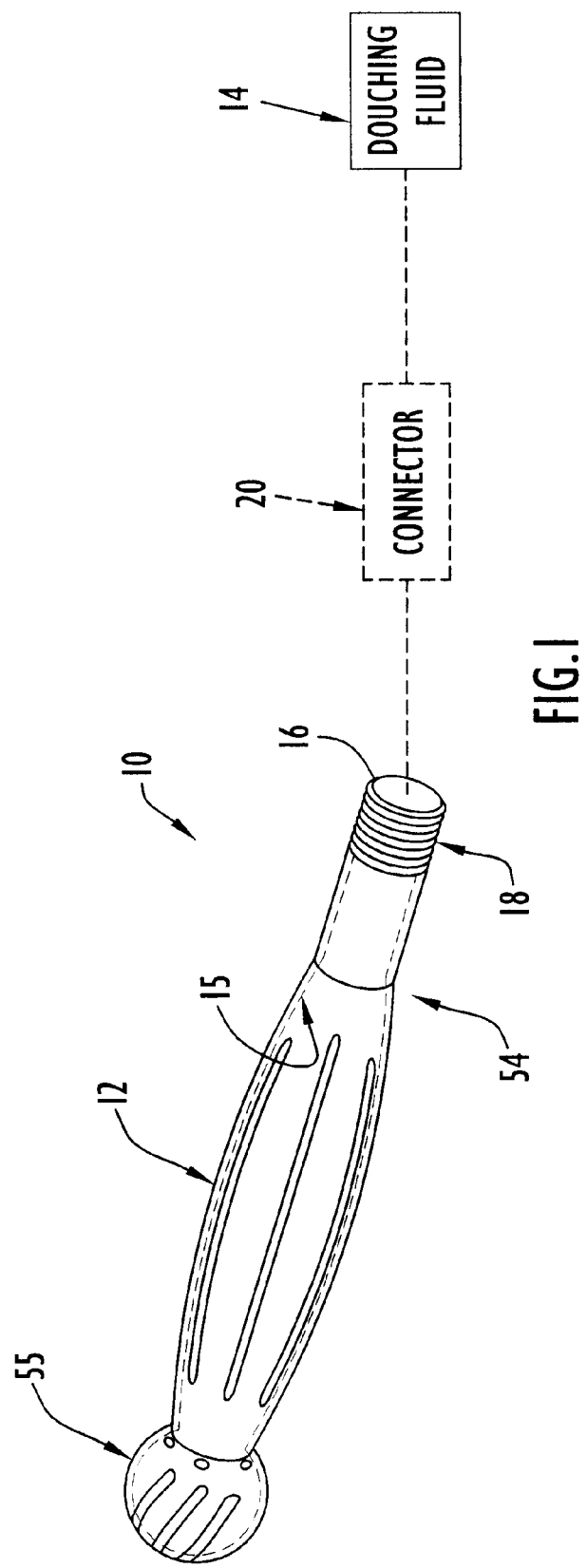
FIG. 1 is an exploded perspective view, partly schematic, of a vaginal douche according to the present invention.

An anatomical tissue deodorizer according to the present invention is illustrated in FIG. 1 as a vaginal douche 10. Vaginal douche 10 comprises a vaginal douche applicator 12 and a source or supply 14 of douching fluid coupled with vaginal douche applicator 12. The vaginal douche applicator 12 has a longitudinal passage or lumen 15 therein for being supplied with douching fluid from the source or supply 14. An open proximal end 16 of the vaginal douche applicator 12 provides communication with the passage 15 and may include securing structure 18 to facilitate coupling of the vaginal douche applicator with the source or supply 14. The source or supply 14 may be any suitable source or supply of water, preferably gravity fed from a container, with or without therapeutic additives. A connector 20 may be used to couple the vaginal douche applicator 12 with the source or supply 14, and the design of the connector 20 can vary depending on the source or supply 14. As described further below, the vaginal douche applicator 12 is designed for repeated use.

Figure 2:
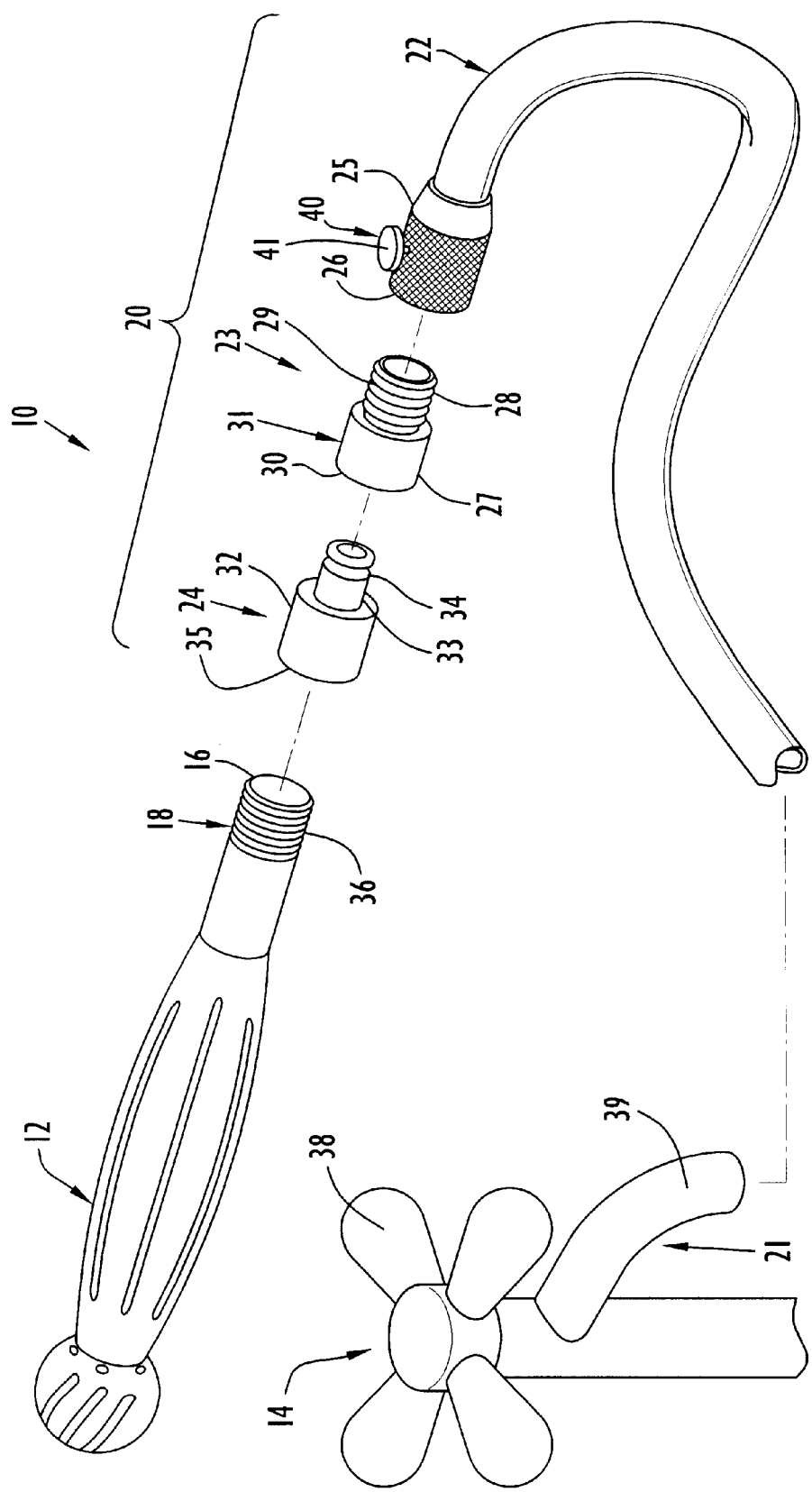
FIG. 2 is an exploded perspective view depicting one version of the vaginal douche.

In one version of vaginal douche 10 illustrated in FIG. 2, connector 20 is designed to couple the vaginal douche applicator 12 with a standard tap or faucet 21 forming the source or supply 14 of douching fluid. The connector 20 is shown exploded in FIG. 2 and comprises a fluid supply conduit 22, a coupling 23 and an adaptor 24. The fluid supply conduit 22 may be designed in many various ways as a hollow conduit, including various tubes and hoses, and is preferably flexible for ease of use. The fluid supply conduit 22 has a proximal end (not shown) releasably connectable with the tap or faucet in a conventional manner and has a distal end carrying a hollow fitting 25. Fitting 25 may have a knurled external surface to facilitate grasping and has an open distal end 26 with an internal thread (not visible in FIG. 2) for releasable threaded connection to coupling 23.

Coupling 23 is hollow and includes a relatively larger diameter cylindrical distal section 27 and a relatively smaller diameter cylindrical proximal section 28 coaxially aligned with distal section 27. Proximal section 28 has an external diameter to fit within the distal end 26 of fitting 25 and has an external thread 29 for releasably, threadedly engaging the internal thread of fitting 25. Distal section 27 includes an open distal end 30 and a longitudinally slidable collar or sleeve 31 biased by an internal spring (not shown) of coupling 23 to be normally disposed in a locking position, shown in FIG. 2, in which one or more detents (not shown), such as balls, within the distal section 27 are held in a radially inward position to protrude into the lumen or interior of the distal section 27. The collar 31 is manually moveable or slidable longitudinally from the locking position to a release position in which the one or more detents are free to move radially outwardly into the wall of distal section 27 so that the one or more detents no longer protrude into the lumen or interior of the distal section 27. When the collar 31 is thereafter released, the collar 31 is automatically returned to the locking position due to the bias of the internal spring, and the one or more detents are also automatically returned to the radially inward position.

The adaptor 24 is hollow and includes a cylindrical distal portion 32 and a cylindrical stem 33 extending proximally from distal portion 32 in coaxial alignment therewith. Stem 33 has an external diameter to fit within the open distal end 30 of coupling 23 and has an external annular or circumferential groove 34. When the collar 31 is in the locking position, protrusion of the one or more detents into the lumen or interior of coupling 23 prevents full insertion of stem 33 into the distal section 27. When the collar 31 is moved to the release position, the stem 33 is able to be fully inserted into the distal section 27 since the one or more detents move radially outwardly and retract into the wall of the distal section 27. Insertion of stem 33 as far as possible into distal section 27 corresponds with alignment of groove 34 with the one or more detents. Accordingly, when the collar 31 thereafter returns to the locking position, the one or more detents are returned to the radially inward position and enter the groove 34. In this manner, the adaptor 24 is releasably connected to the coupling 23 and is releasably locked thereto. The distal portion 32 of adaptor 24 has an open distal end 35 with an internal thread (not visible in FIG. 2), and the lumen or interior of distal portion 32 is of a size to receive the proximal end 16 of vaginal douche applicator 12 in the open distal end 35 of distal portion 32. The securing structure 18 of vaginal douche applicator 12 includes an external thread 36 for releasable threaded engagement with the internal thread of distal portion 32.

The tap or faucet 21 conventionally includes a built-in valve, operable via a knob 38, for controlling fluid flow from a spigot 39. Accordingly, the tap or faucet may be used to selectively control, limit or regulate the force, pressure and/or volume of douching fluid flow supplied to the vaginal douche applicator. However, a more desirable and safer way to control, limit or regulate the force, pressure and/or volume of douching fluid flow from tap or faucet 21 into applicator 12 is a valve or other flow controlling, flow limiting or flow regulating structure provided in or on the applicator and/or the connector. Where a valve is provided in or on the connector shown in FIG. 2, the valve may be provided in or on any of the components of the connector including the fluid supply conduit 22, the coupling 23 and the adaptor 24.

As an example, FIG. 2 illustrates a valve 40 incorporated in the fitting 25 of fluid supply conduit 22. Valve 40 includes an operating member 41 connected to a valve body (not shown) disposed in the lumen or passage of fitting 25. The valve body is spherical and fills the cross-sectional dimension of the lumen or passage of the fitting 25. The valve body has a plurality of intersecting flow passages extending diametrically therethrough, with the flow passages being of different cross-sectional diameters or sizes. The operating member 41 forms an externally located knob or handle that is manually rotatable to correspondingly rotate the valve body about an axis perpendicular to a central longitudinal axis of the fitting 25 to axially align a selected one of the flow passages with the central longitudinal axis of fitting 25. When one of the flow passages is aligned with the central longitudinal axis of the fitting, the remaining flow passage or passages is/are blocked or obstructed by an internal surface of the fitting. The flow passage that is axially aligned with the central longitudinal axis of fitting 25 forms part of and dictates the cross-sectional size of the lumen or passage of fitting 25. In this manner, the operating member 41 is operable to selectively adjust the cross-sectional size of the lumen or passage of fitting 25, thereby controlling, limiting or regulating fluid flow through the fitting 25 into the coupling 23. Visual and/or tactile indicia can be provided at any suitable location or locations to indicate the rotational positions for the operating member 41 corresponding to alignment of the flow passages, respectively, with the central longitudinal axis of fitting 25. Of course, each rotational position for the operating member should correspond to a safe force, pressure and/or volume of douching fluid flow into the vaginal douche applicator to ensure that douching fluid discharged from the vaginal douche applicator is not forced into the cervical canal. The same indicia used to indicate the rotational positions for the operating member, or different visual and/or tactile indicia provided at any suitable location or locations, may be used to provide an indication of the flows, pressures and/or volumes corresponding to the rotational positions, respectively.

The fluid supply conduit 22, the coupling 23 and the adaptor 24 may be the same as or similar to those disclosed in U.S. Pat. No. 6,190,365 B1, to Abbott et al, the entire disclosure of which is incorporated herein by reference. It should be appreciated that the source or supply 14, including a gravity feed container, can be coupled directly to the vaginal douche applicator 12 without a connector as represented in FIG. 1. The fluid supply conduit 22 can be designed for direct connection to the vaginal douche applicator 12 or to the adaptor 24 and either or both of the adaptor 24 and the coupling 23 can be eliminated. The fluid supply conduit 22 can be of any desired length. In addition, a container containing one or more therapeutic substances or other additives can be coupled between the vaginal douche applicator 12 and the source 14 of douching fluid, as described in the application incorporated herein by reference, for introducing a desired quantity of such one or more additives into the water being used as the douching fluid. The fluid supply conduit 22, the coupling 23, and/or the adapter 24 may be disposable but are preferably reusable for convenience and economy. The fluid supply conduit 22, the coupling 23 and/or the adapter 24 may thusly be made of materials which facilitate cleanliness or sterility.

Figure 3:
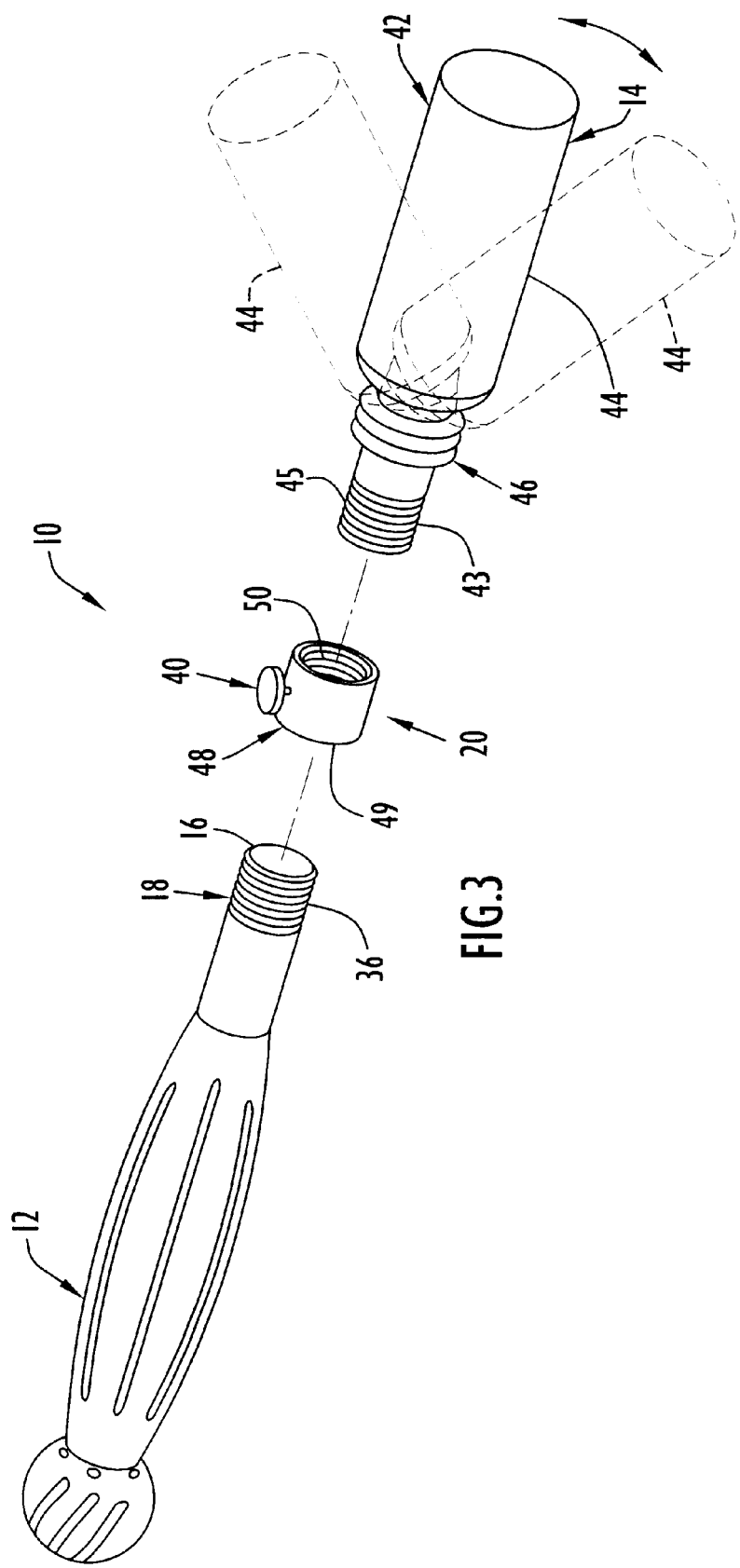
FIG. 3 is an exploded perspective view depicting another version of the vaginal douche.

In another version of vaginal douche 10 illustrated in FIG. 3, the connector 20 is designed to couple the vaginal douche applicator 12 with a container, bottle or bag 42 forming the source or supply 14 of douching fluid. The container 42 contains douching fluid and has a neck 43 extending from a container body 44 to terminate at an open end of container 42. An external thread 45 is disposed on neck 43 adjacent or close to the open end of container 42, and the neck 43 is connected to the container body 44 at a flexible junction 46. Flexible junction 46 allows the container 42 to bend or pivot at junction 46 so that the container body 44 can be selectively angled relative to the vaginal douche applicator 12 for versatility and ease of use. FIG. 3 shows the container 42 in a first position in which the container body 44 is in longitudinal or axial alignment with the neck 43 so that the container body is also in longitudinal or axial alignment with the connector 20 and with the vaginal douche applicator 12. As shown by an arrow in FIG. 3, the container body 44 can be pivoted or rotated about junction 46 to a variety of second positions, two of which are represented in dotted lines, in which the container body is no longer longitudinally or axially aligned with the neck 43 so that the container body is also no longer in longitudinal or axial alignment with the connector 20 and with the vaginal douche applicator 12. As shown by the second positions illustrated in FIG. 3, the container body 44 may be disposed at a desired angle to a central longitudinal axis of the vaginal douche applicator 12.

In one of the second positions depicted in FIG. 3, the container body 44 is pivoted upwardly to facilitate establishment of gravity feed of douching fluid from the container 42 into the vaginal douche applicator 12.

The junction 46 is shown as comprising one or more expandable and collapsible pleats formed integrally, unitarily with the container 42, but can be designed in any suitable manner integrally, unitarily with the container or as one or more separate components. Also, the location of junction 46 on the container 42 can be varied. The junction 46 allows the container body 44 to be positioned as needed to facilitate establishment of gravity feed of the douching fluid contained therein into applicator 12. Alternatively or additionally, at least the container body 44 may be flexible to permit the container 42 to be manually squeezed, compressed or collapsed to dispense the douching fluid from the open end thereof. However, a gravity feed is preferred for enhanced safety. The container 42 may be reusable but is preferably disposable after use to ensure cleanliness for repeated use by permitting a new container of douching fluid to be coupled with the vaginal douche applicator 12. The container 42 can be coupled directly to the vaginal douche applicator 12, without a connector, as represented by FIG. 1.

In the vaginal douche 10 of FIG. 3, connector 20 comprises a hollow, cylindrical coupling 48 having an open distal end 49 sized to receive the proximal end 16 of vaginal douche applicator 12. The open distal end 49 has an internal thread (not visible in FIG. 3) for releasable threaded engagement with the external thread 36 of vaginal douche applicator 12. The coupling 48 has an open proximal end sized to receive the open end of container 42, and the open proximal end of coupling 48 has an internal thread 50 for releasable threaded engagement with the external thread 45 of container 42. Coupling 48 includes a valve 40 for selectively controlling the cross-sectional size of the passage or lumen through the coupling 48 in order to selectively control, limit or regulate the force, pressure and/or volume of douching fluid flow from container 42 into the vaginal douche applicator 12. The coupling 48 can be reusable or can be disposable. It is preferred that a reusable coupling be made of a material conducive to cleaning.

Figure 4:
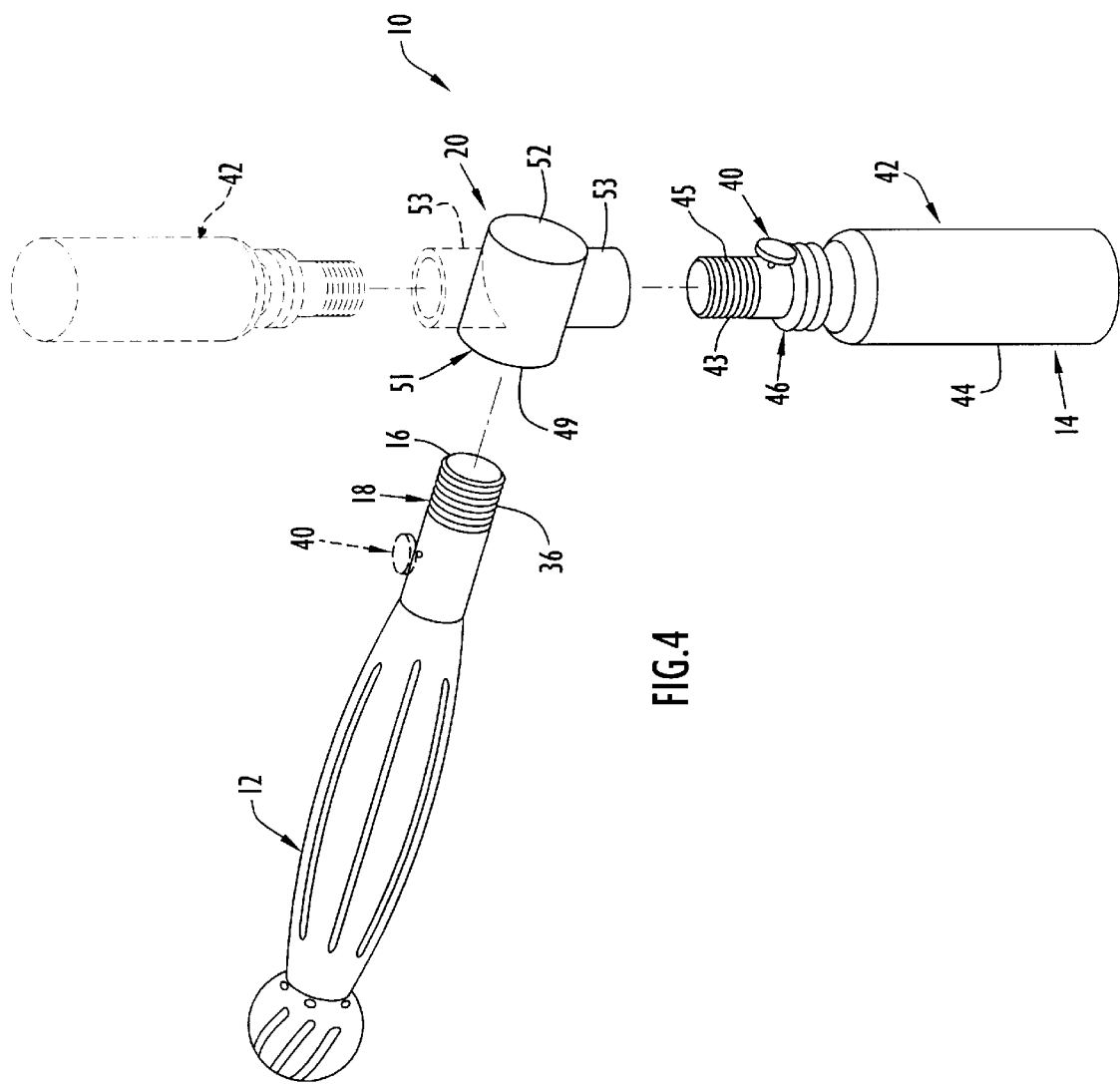
FIG. 4 is an exploded perspective view depicting an additional version of the vaginal douche.

An additional version of vaginal douche 10 is depicted in FIG. 4, in which the connector 20 connects the container 42 to the vaginal douche applicator 12 in a longitudinally offset position. Connector 20 as illustrated in FIG. 4 comprises a hollow coupling 51, which is similar to coupling 48 but has a closed proximal end 52 and a hollow, transverse extension 53. Transverse extension 53 extends perpendicularly from a cylindrical body of coupling 51 and terminates at an open end provided with an internal thread (not visible in FIG. 4). The neck 43 of container 42 fits into the open end of extension 53 with the external thread 45 of container 42 in releasable engagement with the internal thread of extension 53. The cylindrical body of coupling 51 has a central longitudinal axis perpendicular to extension 53, and the interior of the cylindrical body is in communication with the interior of extension 53. The cylindrical body of coupling 51 has an open distal end for releasable threaded engagement with vaginal douche applicator 12 as described for coupling 48. Accordingly, when the container 42 is coupled with the vaginal douche applicator 12 via coupling 51, the container 42 is disposed in a first position perpendicular to the central longitudinal axis of the vaginal douche applicator. However, the angle of the container body 44 with the vaginal douche applicator can be varied by moving the container to a second position in which the container body is pivoted around junction 46. As shown in FIG. 4, the container body 44 may, as an example, be oriented to extend upwardly or downwardly relative to the vaginal douche applicator 12. By orienting the container body 44 to extend upwardly as shown in dotted lines, gravity feed of douching fluid from the container into the vaginal douche applicator can be facilitated. FIG. 4 also illustrates valve 40 provided at neck 43 to control, limit or regulate fluid flow entering the vaginal douche applicator 12. As shown in dotted lines, valve 40 could be provided at the proximal end of the vaginal douche applicator 12.

Vaginal douche applicator 12 preferably has a stainless steel external surface as described in the patent incorporated herein by reference. As best illustrated in FIGS. 1 and 5–10, vaginal douche applicator 12 comprises an applicator body 54 having open proximal end 16 and a forward end formed as, joined to or connected with a head or tip 55. Proximal end 16 provides communication with the lumen or passage 15 which extends within applicator body 54 and head 55 as shown in dotted lines in FIG. 1. The passage 15 is supplied with douching fluid from the source or supply 14 with which the proximal end of the vaginal douche applicator is coupled. The passage 15 extends distally from the open proximal end 16 to terminate at an internal distal end surface within head 55. The passage 15 has a central longitudinal axis coaxial with the central longitudinal axis of vaginal douche applicator 12. Head 55 is coaxial with the applicator body 54 and is defined by a wall 56 forming a closed distal end for the vaginal douche applicator, the wall 56 having a substantially spherical external configuration. The center of head 55 is located along the central longitudinal axis of the vaginal douche applicator 12 and is contained in a solid central area 57 of wall 56 shown in FIG. 8.

Applicator body 54 has a tapered distal segment 58 extending proximally from head 55 and a cylindrical proximal segment 60 extending proximally from a rearward end of distal segment 58. The distal segment 58 has a forward end connected to head 55. Distal segment 58 is circular in external cross-sectional configuration, with the external cross sectional configuration of the distal segment 58 tapering or decreasing toward or in the direction of the forward and rearward ends of the applicator body. In particular, distal segment 58 tapers in external cross-sectional diameter or size forwardly and rearwardly from a maximum external cross-sectional diameter or size at or approximately at the longitudinal center of the distal segment 58 between head 55 and proximal segment 60. The external cross-sectional diameter or size of distal segment 58 tapers relatively gradually closer to the longitudinal center of the distal segment and tapers relatively more steeply closer the forward and rearward ends of the distal segment. The distal segment 58 thusly has a distal external cross-sectional diameter or size adjacent head 55, i.e. at the forward end of distal segment 58, and has a proximal external cross-sectional diameter or size adjacent proximal segment 60, i.e. at the rearward end of distal segment 58. The distal and proximal external cross-sectional diameters or sizes are smaller than the maximum external cross-sectional diameter or size. The distal external cross-sectional diameter or size may be considered a distal minimum external cross-sectional diameter or size, and the proximal external cross-sectional diameter or size may be considered a proximal minimum external cross-sectional diameter or size. The proximal segment 60 has a circular external cross-sectional configuration corresponding to the proximal minimum external cross-sectional diameter or size of distal segment 58. The proximal segment 60 terminates proximally at an opening into proximal end 16, and the external cross-sectional configuration and size of the proximal segment is uniform or constant between distal segment 58 and the opening.

Figure 9:
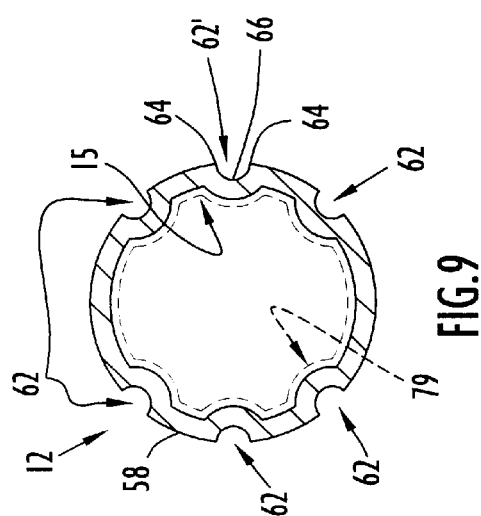
FIG. 9 is a cross-sectional view depicting a lumen or passage of the vaginal douche applicator.

A plurality of external body channels 62 are disposed along the external surface of the distal segment 58. Each body channel 62 is formed by a longitudinally extending groove or flute which follows the external contour of the distal segment 58 and extends in the same direction as the central longitudinal axis of the vaginal douche applicator. Each body channel 62 has a width between a pair of opposing, longitudinally extending side edges 64 and has a curved or radiused bottom surface 66 with a radius of curvature from a point external of the vaginal douche applicator 12 as shown in FIGS. 5 and 9 for body channel 62'. The width and/or depth of each body channel 62 preferably tapers at forward and rearward ends of the body channel such that the forward and rearward ends of the body channels merge or blend into the external surface of the distal segment 58. Each body channel 62 has a length between its forward and rearward ends, with each body channel extending longitudinally or lengthwise along a substantial portion of the length of distal segment 58. The forward ends of body channels 62 are spaced rearwardly from head 55. The rearward ends of body channels 62 may be spaced forwardly from proximal segment 60 as shown for vaginal douche applicator 12 or may extend to the proximal segment as described below for the vaginal douche applicator 212. Each body channel 62 is bisected longitudinally by a radial plane, i.e., a plane radial to the central longitudinal axis of vaginal douche applicator 12, and has a central longitudinal axis disposed in the radial plane. The vaginal douche applicator 12 includes six like channels 62 arranged around the central longitudinal axis of vaginal douche applicator 12. The body channels 62 could be equally spaced or irregularly spaced about the central longitudinal axis of the vaginal douche applicator. In the illustrated embodiment, the body channels 62 are irregularly spaced and are arranged in two groups disposed on opposite sides of the applicator body with each group having three body channels, i.e. a central body channel disposed between two side body channels. Each group of body channels has its side channels spaced a first circumferential distance from its central channel. The side channels of one group are spaced from corresponding side channels of the other group by a second circumferential distance which is greater than the first circumferential distance.

Head 55 is substantially spherical in external configuration with a rearward end 68 joined to the forward end of distal segment 58. The head 55 has an external maximum diametric dimension perpendicular to the central longitudinal axis of vaginal douche applicator 12 that is the same as or substantially the same as the maximum external cross-sectional diameter or size of distal segment 58. A plurality of discharge or outlet holes or passages 70 are formed in wall 56 at the rearward end of head 55 and may thusly be considered rearward or proximal discharge or outlet holes or passages, the rearward discharge holes 70 being disposed close to or adjacent the forward end of distal segment 58. The holes 70, which communicate with the passage 15, are shown as being disposed at, in contact with or in abutment with the forward end of distal segment 58 and are thusly disposed at, in contact with or in abutment with the minimum distal external cross-sectional diameter of distal segment 58. However, the holes 70 can be disposed close to but spaced slightly forwardly from the forward end of distal segment 58. Each hole 70 is shown as having a circular cross-sectional configuration; however, the holes 70 can have a non-circular cross-sectional configuration. Particularly where the holes 70 are at, in contact with or in abutment with the forward end of distal segment 58, the holes 70 may have circular or non-circular cross-sectional configurations including partial and semicircular cross-sectional configurations. Preferably, six holes 70 are provided in head 55 at equally spaced or irregularly spaced radial locations around the distal segment 58 as best shown in FIG. 7, which is representative of irregularly spaced rearward discharge holes. Accordingly, the center of each hole 70 is disposed in a radial plane, i.e., a plane radial to the central longitudinal axis of vaginal douche applicator 12. The holes 70 face proximally and outwardly toward the applicator body 54 and are arranged on head 55 with each hole 70 preferably aligned or substantially aligned in the longitudinal direction with a respective body channel 62 as shown for applicator 12. It should be appreciated, however, that the holes 70 can be offset from the body channels 62 in the longitudinal direction such that each hole may be disposed between a respective pair of adjacent body channels. It should also be appreciated that the number of holes 70 can vary in that more than six holes or less than six holes can be provided in head 55. Depending on the number of holes 70, a hole 70 can be aligned in the longitudinal direction with each body channel 62 as well as there being a hole 70 between each pair of adjacent body channels 62 as described below for vaginal douche applicator 212.

A plurality of external head channels 72 are disposed along the external surface of wall 56. As shown in FIG. 8, the head channels 72 have forward ends disposed around the solid central area 57 of wall 56 which forms the closed distal end of the vaginal douche applicator. Each head channel 72 extends proximally from its forward end to a rearward end, with each head channel 72 extending along a substantial portion of the length of head 55 as measured from the distal end of vaginal douche applicator 12 to the forward end of distal segment 58. The rearward end of each head channel 72 may be aligned or substantially aligned in the longitudinal direction with a forward end of a corresponding body channel 62. Each head channel 72 has a width between opposing side edges 74 and has a curved or radiused bottom surface 76 with a radius of curvature from a point external to the vaginal douche applicator 12 as shown in FIGS. 5 and 8 for head channel 72'. The forward ends and the rearward ends of head channels 72 preferably blend into or merge with the external surface of head 55 as described above for body channels 62. Each head channel 72 is angled from distal to proximal in the same direction such that the head channels 72 have a helical arrangement on head 55. The head channels may be equally spaced or irregularly spaced from one another about the central longitudinal axis of the vaginal douche applicator, with central longitudinal axes of the head channels 72 contained in planes P, respectively, disposed at a helix angle A to the plane containing the central longitudinal axis of the vaginal douche applicator 12 as shown in FIG. 5 for head channel 72'. Accordingly, the head channels 72 extend in a direction transverse to the central longitudinal axis of the vaginal douche applicator so that the head channels 72 are transverse to the body channels 62. Also, the planes P are non-radial to the central longitudinal axis of the vaginal douche applicator. When the vaginal douche applicator 12 is viewed from the side with the distal end thereof on the left as shown in FIG. 5, the head channels 72 are angled downwardly from distal to proximal. Six head channels 72 are provided in head 55 with the head channels arranged in two groups of three head channels each on opposite sides of head 55 as described above for body channels 62. Each group of head channels 72 is disposed on a side of head 55 corresponding to a side of applicator body 54 on which a group of body channels 62 is disposed.

Every other or alternate head channel 72 has a forward outlet or discharge hole or passage 78 therein spaced proximally from the solid central area 57 of wall 56 and from the forward ends of the head channels and spaced distally from the rearward discharge holes 70. Forward discharge holes 78 open along the bottom surfaces 76 of the corresponding head channels 72 and communicate with the lumen or passage 15 of vaginal douche applicator 12. The forward discharge holes 78 may be equally spaced or irregularly spaced from one another in a radial or rotational direction, the forward discharge holes 78 being representative of irregularly spaced forward discharge holes. One group of head channels 72 has a forward discharge hole located in its central head channel while the other group of head channels 72 has a forward discharge hole in each of its side head channels as best depicted in FIG. 8. The forward discharge holes face distally and face outwardly from head 55 at angle A, which may be considered a helix angle or transverse angle, to the central longitudinal axis of the vaginal douche applicator. The diameter or cross-sectional size of forward discharge holes 78 is sufficiently large to ensure a relatively low pressure flow of douching fluid therefrom as explained further below. The forward discharge holes 78 may have circular or non-circular cross-sections.

FIGS. 1 and 9 illustrate passage 15 as being of non-uniform or variable cross sectional configuration and size along the entire length thereof. It should be appreciated, however, that the cross-sectional configuration and size of passage 15 can be uniform or constant between proximal end 16 and the internal distal end surface. In the case of non-uniform passage 15, the lumen or passage 15 has a cross-sectional configuration corresponding to the external cross-sectional configuration of the applicator body 54 in that the wall of the vaginal douche applicator 12 is of uniform thickness throughout. The vaginal douche applicator 12 may have an internal coating or finish 79 along the internal wall or surface that defines passage 15 as represented by dotted lines in FIG. 9. Internal coating or finish may be a germ-resistant coating or finish or any other coating or finish that facilitates cleanliness and hygiene, preferably preserving cleanliness of the vaginal douche applicator interior between uses. A particularly preferred internal coating is an antimicrobial internal coating. An internal coating may comprise an impregnation or dispersal of one or more selected substances or elements in the material used to form the internal surface or wall or may comprise a discrete surface coating of one or more selected substances or elements over or upon the internal surface or wall. An internal finish may comprise one or more characteristics obtained from various finishing processes including mechanical, chemical, electrical and thermal finishing processes. Representative antimicrobial substances which may be used as an internal coating include AGION silver ion complex and copper alloy. A representative internal finish is electro polishing which, where the internal surface is stainless steel, further enhances the smooth and slippery characteristics of the stainless steel internal surface so that bacteria slide off and cannot take hold to colonize.

Figure 10:
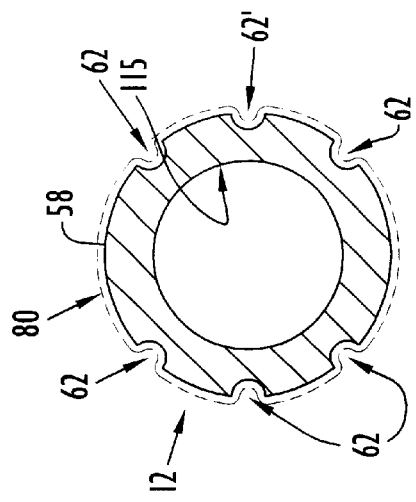
FIG. 10 is a cross-sectional view depicting an alternative lumen or passage for the vaginal douche applicator.

FIG. 10 illustrates the vaginal douche applicator 12 with an alternative lumen or passage 115 of uniform or constant cross-sectional configuration and size. In the case of passage 115, the wall forming the vaginal douche applicator 12 is of non-uniform cross-sectional thickness as depicted in FIG. 10. FIG. 10 also illustrates the vaginal douche applicator 12 with an optional external coating or finish 80, shown in dotted lines, which may be the same as the internal coating or finish described above. The external finish should be a steel passivazation first followed by electro polishing.

In a preferred embodiment of vaginal douche applicator 12, the vaginal douche applicator is about 6.0 inches long from its distal end to its proximal end 16, with the proximal segment 60 being about 0.50 inch in length, the distal segment 58 being about 4.63 inches in length, and the head 55 being about 0.87 inch in length. The maximum external cross-sectional diameter of distal segment 58 and the external diametric dimension of head 55 is about 0.93 inch, with the maximum external cross-sectional diameter of distal segment 58 being located about 2.01 inches proximally from head 55. The distal minimum external cross-sectional diameter is about 0.50 inch, and the proximal minimum cross-sectional diameter is about 0.31 inch. Body channels 62 have a length of about 2.35 inches, with the length of body channels 62 being centered or substantially centered within the length of the distal segment 58. Body channels 62 and head channels 72 have a maximum width of about 0.12 inch and a depth of about 0.06 inch. The radius of curvature for the bottom surfaces 66 and 76 is about 0.06 inch. The helix angle A is 30°. The rearward discharge holes 70 have a diameter of about 0.06 inch, and the forward discharge holes 78 have a diameter of about 0.09 inch. The forward discharge holes 78 are located about 0.23 inch proximally of the distal end of the vaginal douche applicator. The first circumferential distance is about 0.48 inch and the second circumferential distance is about 0.53 inch. The vaginal douche applicator has a uniform wall thickness of about 0.01 inch.

Figure 11:
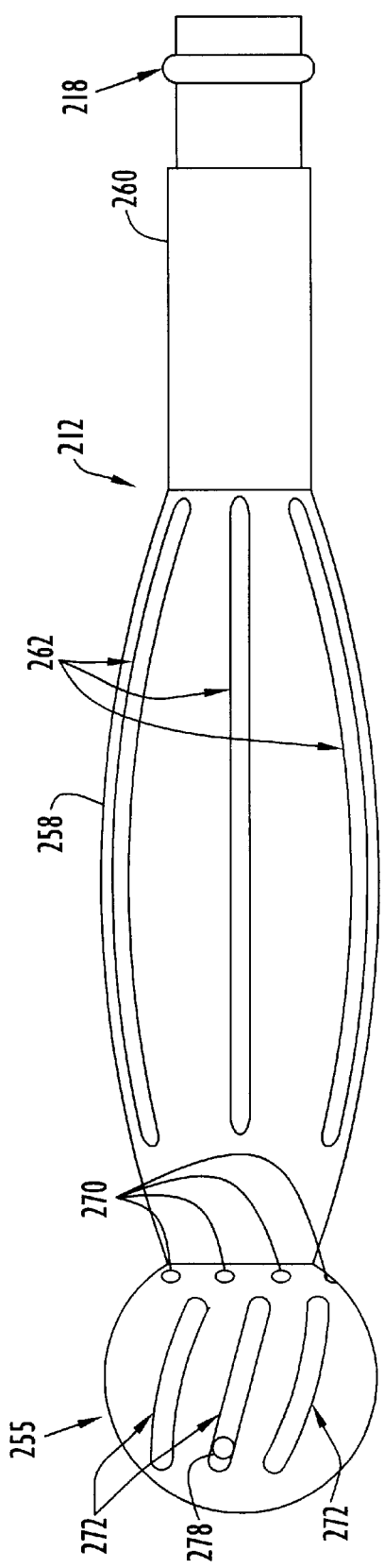
FIG. 11 is a side view of an alternative vaginal douche applicator according to the present invention.

An alternative vaginal douche applicator according to the present invention is illustrated in FIG. 11 at 212. Vaginal douche applicator 212 is similar to vaginal douche applicator 12 with the exception that the maximum cross-sectional diameter of distal segment 258 and the external maximum diametric dimension of head 255 are larger than that for vaginal douche applicator 12. Also, head 255 and proximal segment 260 for vaginal douche applicator 212 are greater in length than head 55 and proximal segment 60. The body channels 262 for vaginal douche applicator 212 are different from body channels 62 in that the rearward ends of channels 262 extend to the proximal segment 260. In addition, head 255 has a greater number of rearward discharge holes 270. The securing structure 218 for vaginal douche applicator 212 is different than securing structure 18 and comprises an annular boss. In a preferred embodiment for vaginal douche applicator 212, the vaginal douche applicator 212 is about 6.0 inches long. The maximum external cross-sectional diameter for distal segment 258 and the maximum external diametric dimension for head 255 are about 1.2 inches. Head 255 is about 1.0 inch long, and distal segment 258 is about 3.375 inches long. Preferably, eight rearward discharge holes 270 are provided in vaginal douche applicator 212, with the rearward end of each head channel 272 disposed between a pair of adjacent rearward discharge holes 270.

The vaginal douches and vaginal douche applicators according to the present invention are used in methods of vaginal douching and deodorization. As described by way of example for vaginal douche 10, the vaginal douche applicator 12 is coupled with the source or supply 14 of douching fluid (not shown in FIG. 12), which will typically be only water for routine use. The use of water alone as the douching fluid ensures minimal alteration of vaginal pH while washing out bacteria and sperm. However, the douching fluid may include additives, such as pH lowering substances, to inhibit growth of non-acid loving bacteria. A culture of lactobacilli, such as "Luck Lacto's" could be added to the douching fluid to assist lactobacilli proliferation and offset the washout of beneficial bacteria. Other additives which may be added to the douching fluid include pH altering substances, antiseptic substances, antimicrobial substances, antibiotics, probiotics and/or microbicides. Any of the foregoing additives or substances could be applied to the vaginal canal subsequent to douching using the vaginal douche applicator to apply the additives or substances as explained further below.

Figure 12:
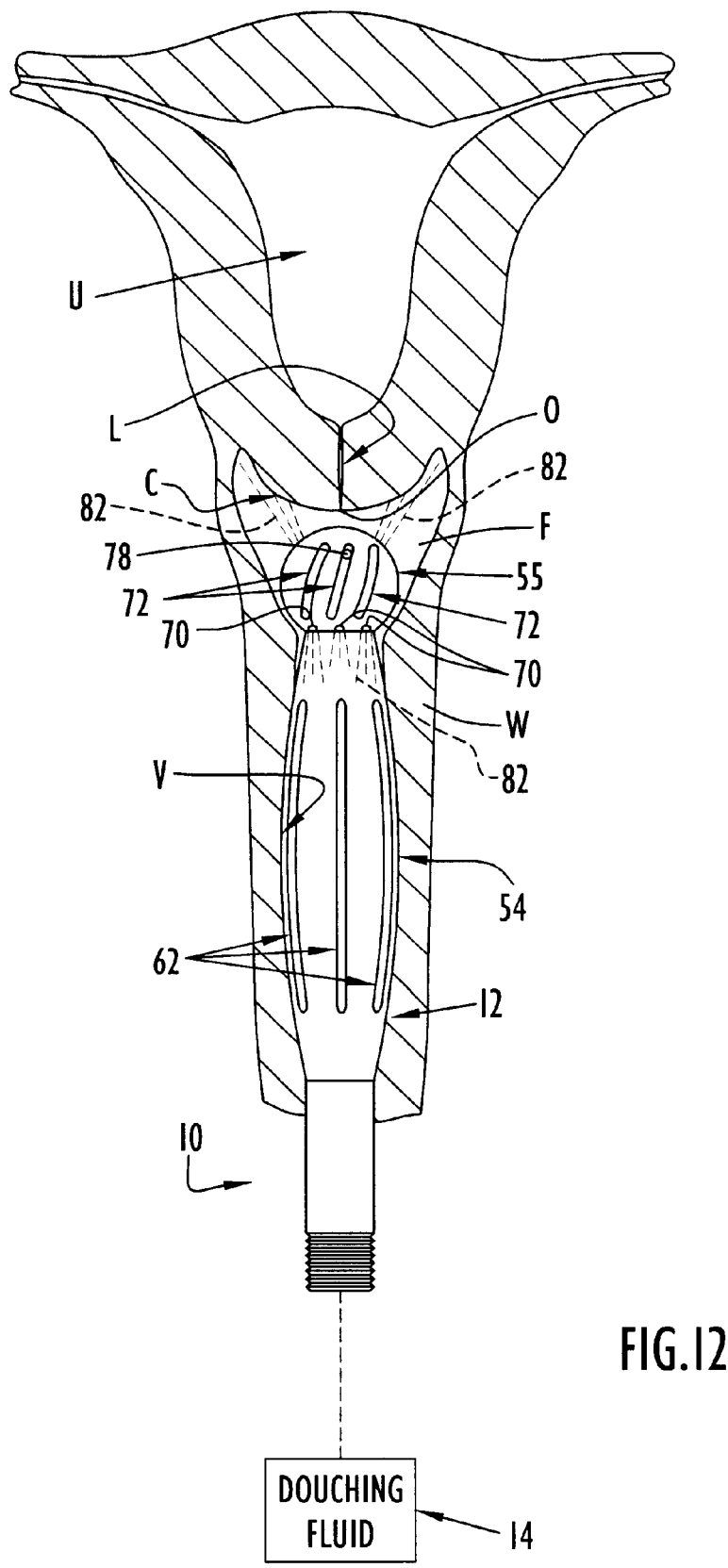
FIG. 12 is a broken view, partly in section, illustrating use of the vaginal douche in a method of vaginal douching or deodorization according to the present invention.

Once the vaginal douche applicator 12 is coupled with the source or supply 14 of douching fluid, the distal end of the vaginal douche applicator 12 is inserted through the vaginal opening into the vaginal canal V. The vaginal douche applicator 12 is advanced into the vaginal canal to a comfortable, safe insertion distance in which the head 55 is disposed within or adjacent the upper portion or fornix F of the vaginal canal V as shown in FIG. 12. In this position, the solid central area 57 of head 55 is aligned or substantially aligned with the cervical os O leading into the cervical canal L. The vaginal wall W produces a "squeegee" effect around the head 55 during insertion of the vaginal douche applicator 12 in the vaginal canal V, thusly providing a self-cleaning effect which deters the transfer of harmful or undesirable organisms from the lower portion to the upper portion of the vaginal canal. The configuration and contour of the applicator body 54 expands the vaginal canal V and maximizes the surface area of vaginal tissue and mucosa in contact with the stainless steel external surface along an interface between the vaginal wall W and the vaginal douche applicator 12. Accordingly, the reaction of the stainless steel with odor linked chemical bonds will also be maximized. Although contact between the vaginal douche applicator 12 and the vaginal wall W is maximized, the vaginal douche applicator 12 maintains a "leaky" or non-fluid tight seal or fit with the vaginal wall. In particular, the body channels 62 prevent a successful or complete seal of vaginal wall W around the external surface of the vaginal douche applicator 12, no matter how tightly the vaginal wall clamps down on the vaginal douche applicator.

Douching fluid from the source or supply 14 is supplied to the lumen or passage 15 through the open proximal end 16 of the vaginal douche applicator 12, and the douching fluid exits or is discharged from the vaginal douche applicator into the vaginal canal V through the rearward and forward discharge holes 70 and 78. As discussed above, flow of douching fluid into the vaginal douche applicator 12 can be controlled, regulated or limited via valves or other flow regulating structure and/or gravity feed containers, thereby preventing discharge of douching fluid from the applicator at pressures high enough to force the douching fluid into the cervical canal L of cervix C.

As shown in FIG. 12, douching fluid 82 is discharged from rearward discharge holes 70 and forward discharge holes 78 as drizzle rivulets effecting a drizzle flow effect from head 55 at a low rate and pressure. The douching fluid 82 discharged from the rearward discharge holes 70 into the vaginal canal V creates a sheeting effect over the stainless steel external surface of the vaginal douche applicator, as facilitated by the tapered external contour of applicator body 54. The sheeting effect that is created from the rearward discharge holes 70 floods the external surface of the applicator body 54 with optimally directed, low pressure douching fluid flow along the interface between the vaginal wall W and the applicator body 54. Consequently, the stainless steel external surface of the applicator body 54 is maximally surface flooded with a thin film of douching fluid, and the tissue/steel interface is maximally flooded to enhance reaction of the stainless steel external surface with the vaginal tissue. The vaginal douche applicator 12 also achieves very low pressure washing of the fornix F and the cervix C. The angle of forward discharge holes 78 from the central longitudinal axis of the vaginal douche applicator 12 prevents douching fluid 82 discharged from the forward discharge holes 78 from directly impacting the cervical os O. Also, the solid central area 57 of head 55 acts as a barrier to isolate the cervical os O so that douching fluid does not directly impact the cervical os and enter the cervical canal L. The douching fluid 82 discharged from forward discharge holes 78 is discharged at an angle to the cervical os O and is directed toward and streams off of the sides of the cervix C into and along the vaginal wall forming fornix F, thereby washing the upper portion of the vaginal canal V. Since the cervix C and fornix F are gently washed, cervical and vaginal secretions are diluted and/or flushed from the vaginal canal V.

Discharged douching fluid 82 streams back to head 55 and is directed along head channels 72 to the body channels 62. Discharged douching fluid 82 is directed along the body channels 62 toward the vaginal opening for exit from the vaginal canal V. The body channels 62 and head channels 72 thusly maintain a gravitational rinsing or cleansing flow of douching fluid 82 out of the vaginal canal V. The gravitational flow should be established by the user's body position; for example, the douching method should be preformed while standing or sitting upright so that the user's torso is upright or erect. The flow of douching fluid 82 out of the vaginal canal V flushes or rinses desquamated cells, debris, sperm, bacteria and other undesirable organisms from the vaginal canal. Since a retrograde or gravitational flow of douching fluid from the vaginal canal V is maintained, flow of douching fluid 82 toward the cervix C, particularly the cervical canal L, is minimized so that douching fluid and organisms carried thereby are prevented from being driven upwardly from the lower portion of vaginal canal V to the cervix C. In addition, the channels 62 and 72 prevent douching fluid from becoming trapped and accumulating or building up in the vaginal canal V.

In a representative method, approximately 32 ounces of douching fluid is discharged into the vaginal canal during douching and, upon completion of douching, the vaginal douche applicator 12 is withdrawn from the vaginal canal V. The vaginal douche applicator is cleaned on the inside and on the outside, and soap and water can be used for cleaning. The vaginal douche applicator 12 may then be stored for future or repeated use on demand. The vaginal douche applicator 212 is used in essentially the same manner as that described for applicator 12.

As described in the patent incorporated herein by reference, vaginal odors are neutralized due to contact of the stainless steel external surfaces of the vaginal douche applicators with vaginal tissue in the presence of water. In particular, contact of the stainless steel external surfaces of the vaginal douche applicators 12, 212 with the vaginal tissue in the presence of water causes ionization or chemical reactions with odor linked chemical bonds that results in breakage of the odor linked chemical bonds and neutralization of their odor carrying capabilities. Since it is desirable to preserve the lactobacilli, additives can be used during or subsequent to douching to encourage the growth of lactobacilli as discussed above. In addition to neutralizing vaginal odors, the vaginal douches, the vaginal douche applicators and the methods of vaginal douching and deodorization can be used as a preventative or treatment for bacterial vaginosis, particularly when douching is performed post-coital. Post-coital douching in accordance with the present invention removes sperm from the vaginal canal V, thereby maintaining a lower pH and thusly inhibiting coccoid production. Vaginal douching according to the present invention in the presence of bacterial vaginosis flushes coccoid bacteria and lactobacillus bacteria from the vaginal canal V, thusly lowering the coccoid population to more normal levels and allowing the lactobacilli population to proliferate until a balance is achieved.

Subsequent to douching, the vaginal douche applicators can be used as applicators to introduce or apply one or more therapeutic substances in the vaginal canal V. Representative therapeutic substances include lactobacilli, pH lowering, pH increasing, antiseptic, antibiotic, probiotic and/or microbicides substances. The therapeutic substances may be provided as a treatment fluid of various viscosities including gels. A preselected quantity or dose of treatment fluid may be provided in a container, such as container 42, capable of being coupled with the vaginal douche applicator 12, 212. The treatment fluid is supplied to the lumen or passage of vaginal douche applicator 12, 212 introduced in the vaginal canal V. As described above for douching fluid 82, the treatment fluid is discharged into the vaginal canal V, and the vaginal douche applicator 12, 212 provides a smearing or spreading effect such that the treatment fluid is widely and uniformly dispersed in the vaginal canal. After the treatment fluid has been dispersed in the vaginal canal V, the vaginal douche applicator 12, 212 is withdrawn from the vaginal canal and cleaned for future use.

The vaginal douche applicators of the present invention can be made in their entireties of stainless steel or can be provided with external surface layers of stainless steel. Although it is desirable for the vaginal douche applicators to have external surfaces of stainless steel in order to achieve effective deodorization from contact of the stainless steel with the vaginal tissue in the presence of water, it should be appreciated that the external surfaces of the vaginal douche applicators do not have to be made of stainless steel. Accordingly, the vaginal douche applicators can be made in their entireties or can be provided with external surface layers of plastic and/or other materials including rubber, titanium, copper alloy steel, copper, silver and nickel alloy, for example. The applicator bodies can be formed integrally, unitarily with the heads, or the applicator bodies and heads can be formed as separate components. The vaginal douche applicators are constructed without any sharp edges or corners to avoid injury or trauma to anatomical tissue. Various seals can be used in any of the components of the vaginal douches to prevent or deter leakage. Many various types of valves and/or other flow regulating structures can be used in any of the components of the vaginal douches to control fluid flow including ball cock valves and flapper valves. The valves can be pre-set to obtain a preselected flow rate or can be adjustable by the user to obtain variable flow rates. The stainless steel external surfaces of the vaginal douche applicators are inert, biocompatible and mildly antiseptic to bacteria. The vaginal douche applicators are reusable and are, therefore, inherently less expensive than disposable vaginal douche applicators. Reusability of the vaginal douche applicators promotes more frequent douching, particularly post-coital douching, since the applicators remain available for use on demand and eliminate the need for advanced planning and purchases. The stainless steel external surfaces, particularly where electro polished, are non-porous, smooth and slippery such that maintaining cleanliness of the vaginal douche applicators between uses is facilitated.

In as much as the present invention is subject to various modifications, additions or changes in detail, the preferred embodiments described herein should be considered illustrative only and should not be taken in a limiting sense since various modifications can be made thereto without departing from the scope of the invention as defined by the appended claims.

What is claimed is:

1. A vaginal douche applicator comprising
an applicator body for introduction in the vaginal canal and comprising a central longitudinal axis defining a central longitudinal axis for said vaginal douche applicator, an open rearward end defining an open proximal end for said vaginal douche applicator, a forward end and a plurality of external body channels along an external surface of said applicator body, said body channels extending longitudinally along said applicator body in the same direction as said central longitudinal axis of said vaginal douche applicator;
a head disposed at said forward end of said applicator body and defining a closed distal end for said vaginal douche applicator, said head comprising a plurality of rearward discharge holes, a plurality of forward discharge holes and a plurality of external head channels along an external surface of said head, said rearward discharge holes being disposed at spaced locations about said central longitudinal axis of said vaginal douche applicator and facing proximally toward said applicator body, said forward discharge holes being disposed distally of said rearward discharge holes at spaced locations about said central longitudinal axis of said vaginal douche applicator, said forward discharge holes facing distally and outwardly from said head at an angle to said central longitudinal axis of said vaginal douche applicator, said head channels extending along said head in a direction transverse to said central longitudinal axis of said vaginal douche applicator; and
an internal passage extending through said applicator body to terminate within said head, said open rearward end and said rearward and forward discharge holes being in communication with said passage, said proximal end of said vaginal douche applicator being connectable with a source of douching fluid whereby douching fluid is supplied to said passage for discharge into the vaginal canal through said rearward and forward discharge holes.

2. A vaginal douche applicator as recited in claim 1 wherein said head has a substantially spherical external configuration.

3. A vaginal douche applicator as recited in claim 1 wherein said forward outlet holes face outwardly from said head at an angle of 30° to said central longitudinal axis of said vaginal douche applicator.

4. A vaginal douche applicator as recited in claim 1 wherein each of said forward outlet holes is disposed in a respective one of said head channels.

5. A vaginal douche applicator as recited in claim 4 wherein each of said head channels is disposed at an angle of 30° to said central longitudinal axis of said vaginal douche applicator.

6. A vaginal douche applicator as recited in claim 1 wherein said external surfaces are stainless steel.

7. A vaginal douche applicator as recited in claim 1 wherein said plurality of body channels comprises six body channels spaced about said central longitudinal axis of said vaginal douche applicator.

8. A vaginal douche applicator as recited in claim 7 wherein said plurality of rearward discharge holes comprises six rearward discharge holes spaced about said central longitudinal axis of said vaginal douche applicator.

9. A vaginal douche applicator as recited in claim 8 wherein said rearward discharge holes are aligned with said body channels, respectively, in a longitudinal direction.

10. A vaginal douche applicator as recited in claim 8 wherein said plurality of head channels comprises six head channels spaced about said central longitudinal axis of said vaginal douche applicator.

11. A vaginal douche applicator as recited in claim 10 wherein said plurality of forward discharge holes comprises three forward discharge holes spaced from one another about said central longitudinal axis of said vaginal douche applicator, each of said forward discharge holes being disposed in an alternative one of said head channels.

12. A vaginal douche applicator as recited in claim 11 wherein each of said head channels is disposed at an angle of 30° to said central longitudinal axis of said vaginal douche applicator.

13. A vaginal douche applicator as recited in claim 2 wherein said head channels are helically arranged on said head.

14. A vaginal douche applicator comprising
- an applicator body for introduction in the vaginal canal and comprising a central longitudinal axis defining a central longitudinal axis for said vaginal douche applicator, an open rearward end defining an open proximal end for said vaginal douche applicator, a forward end and a plurality of external body channels along an external surface of said applicator body, each of said body channels having a central longitudinal axis disposed in a plane radial to said central longitudinal axis of said vaginal douche applicator;
- a head disposed at said forward end of said applicator body and defining a closed distal end for said vaginal douche applicator, said head comprising a plurality of rearward discharge holes, a plurality of forward discharge holes and a plurality of external head channels along an external surface of said head, said rearward discharge holes being disposed close to said forward end of said applicator body at spaced locations about said central longitudinal axis of said vaginal douche applicator and facing proximally toward said applicator body, each of said head channels having a central longitudinal axis contained in a plane non-radial to said central longitudinal axis of said vaginal douche applicator, said forward discharge holes being disposed distally of said rearward discharged holes, each of said forward discharge holes being disposed in a respective one of said head channels; and
- an internal passage extending through said applicator body to terminate within said head, said open rearward end and said rearward and forward discharge holes being in communication with said passage, said proximal end of said vaginal douche applicator being connectible with a source of douching fluid whereby douching fluid is supplied to said passage for discharge into the vaginal canal from said rearward and forward discharge holes.

15. A vaginal douche applicator as recited in claim 14 wherein said applicator body comprises a segment having an external cross-sectional configuration that tapers toward said forward and rearward ends of said applicator body.

16. A vaginal douche applicator as recited in claim 15 wherein said external cross-sectional configuration includes a maximum external cross-sectional size, said head has a maximum external diametric dimension perpendicular to said central longitudinal axis of said vaginal douche applicator and said maximum external cross-sectional size is substantially the same as said maximum external diametric dimension.

17. A vaginal douche applicator as recited in claim 16 wherein said vaginal douche applicator has a length of about 6.0 inches and said maximum external cross-sectional size and said maximum external diametric dimension are about 0.93 inch.

18. A vaginal douche applicator as recited in claim 16 wherein said vaginal douche applicator has a length of about 6.0 inches and said maximum external cross-sectional size and said maximum external diametric dimension are about 1.2 inches.

19. A vaginal douche applicator as recited in claim 14 wherein said rearward outlet holes face proximally from said head and said forward outlet holes face distally and outwardly from said head at an angle.

20. A vaginal douche applicator as recited in claim 19 wherein said forward outlet holes face outwardly from said head at an angle of 30° to said central longitudinal axis of said vaginal douche applicator.

21. A vaginal douche applicator as recited in claim 14 wherein each of said planes containing said central longitudinal axes of said head channels is disposed at an angle of 30° to said central longitudinal axis of said vaginal douche applicator.

22. A vaginal douche applicator as recited in claim 14 wherein said body channels and said head channels have a width of about 0.12 inch and a depth of about 0.06 inch.

23. A vaginal douche applicator as recited in claim 14 wherein said external surfaces are stainless steel.

24. A vaginal douche applicator as recited in claim 14 wherein said rearward discharge holes are located adjacent said forward end of said applicator body.

25. A vaginal douche applicator as recited in claim 14 wherein said applicator body has a length, said body channels extend along a substantial portion of said length of said applicator body, said head has a length, and said head channels extend along a substantial portion of said length of said head.

26. A vaginal douche applicator as recited in claim 14 wherein said passage is defined by an internal surface and further including an anti-microbial coating along said internal surface.

27. A vaginal douche applicator as recited in claim 14 wherein said passage is defined by an internal surface having an anti-microbial finish imparted thereto.

28. A vaginal douche comprising
- a vaginal douche applicator for introduction in the vaginal canal and comprising a central longitudinal axis, an applicator body, a head joined to said applicator body and a passage extending through said applicator body and terminating within said head, said applicator body comprising an open rearward end in communication with said passage, a forward end joined to said head, and a plurality of external body channels extending in the same direction as said central longitudinal axis, said head comprising a plurality of rearward discharge holes in communication with said passage, a plurality of forward discharge holes disposed distally of said rearward discharge holes and in communication with said passage, and a plurality of external head channels extending in a direction transverse to said central longitudinal axis, said rearward discharge holes being adjacent said forward end of said applicator body and facing proximally toward said applicator body, said forward discharge holes facing distally and outwardly from said head at an angle; and a source of douching fluid coupled to said rearward end for being supplied to said passage whereby said douching fluid is discharged into the vaginal canal through said forward and rearward discharge holes.

29. A vaginal douche as recited in claim 28 wherein said vaginal douche applicator has a stainless steel external surface.

30. A vaginal douche as recited in claim 29 wherein said stainless steel external surface is electro polished.

31. A vaginal douche as recited in claim 29 wherein said douching fluid comprises water.

32. A vaginal douche as recited in claim 28 wherein said source of douching fluid comprises a container from which said douching fluid is discharged.

33. A vaginal douche as recited in claim 32 wherein said douching fluid is discharged from said container by gravity.

34. A vaginal douche as recited in claim 28 and further including a connector coupling said source of douching fluid to said rearward end.

35. A vaginal douche as recited in claim 28 and further including a valve for regulating flow of said douching fluid into said passage.

36. A vaginal douche as recited in claim 28 wherein said douching fluid comprises a pH increasing substance.

37. A vaginal douche as recited in claim 28 wherein said douching fluid comprises a pH lowering substance.

38. A vaginal douche as recited in claim 28 wherein said douching fluid comprises an antiseptic.

39. A vaginal douche as recited in claim 28 wherein said douching fluid comprises an antibiotic.

40. A vaginal douche as recited in claim 28 wherein said douching fluid comprises a probiotic.

41. A vaginal douche as recited in claim 28 wherein said douching fluid comprises a microbicide.

42. A method of vaginal douching comprising the steps of
introducing a vaginal douche applicator through the vaginal opening into the vaginal canal;
supplying douching fluid to an internal passage of the vaginal douche applicator;
discharging the douching fluid into the vaginal canal through forward discharge holes in a head of the vaginal douche applicator such that the douching fluid is directed toward the sides of the cervix;
discharging the douching fluid into the vaginal canal through rearward discharge holes in the head such that the douching fluid is directed over a body of the vaginal douche applicator and toward the vaginal opening;
directing discharged douching fluid along external head channels of the head such that discharged douching fluid is directed toward external body channels of the body;
directing discharged douching fluid along the body channels in the direction of the vaginal opening such that discharged douching fluid exits the vaginal opening; and
withdrawing the vaginal douche applicator from the vaginal canal.

43. A method of vaginal douching as recited in claim 42 wherein said steps of discharging and directing are performed while the user's torso is upright.

44. A method of vaginal douching as recited in claim 42 wherein said step of discharging the douching fluid into the vaginal canal through forward discharge holes includes discharging the douching fluid from the forward discharge holes at an angle of 30° to a central longitudinal axis of the vaginal douche applicator.

45. A method of vaginal douching as recited in claim 44 wherein said step of discharging the douching fluid into the vaginal canal through forward discharge holes includes discharging the douching fluid toward the sides of the cervix at low pressure.

46. A method of vaginal douching as recited in claim 44 wherein said step of discharging the douching fluid into the vaginal canal through forward discharge holes includes washing the fornix of the vaginal canal.

47. A method of vaginal douching as recited in claim 42 wherein said step of directing discharged douching fluid along external head channels includes directing discharged douching fluid in a direction transverse to a central longitudinal axis of the vaginal douche applicator.

48. A method of vaginal douching as recited in claim 47 wherein said step of directing discharged douching fluid along the body channels includes directing discharged douching fluid in a direction parallel to the central longitudinal axis of the vaginal douche applicator.

49. A method of vaginal douching as recited in claim 42 wherein said step of supplying includes the step of controlling douching fluid flow into the passage.

50. A method of vaginal douching as recited in claim 42 and further including, subsequent to said step of withdrawing, the steps of cleaning the vaginal douche applicator, storing the vaginal douche applicator and reusing the vaginal douche applicator.

51. A method of vaginal douching as recited in claim 42 and further including, subsequent to said step of withdrawing, the steps of reintroducing the vaginal douche applicator into the vaginal canal, supplying a treatment fluid to the internal passage, discharging the treatment fluid into the vaginal canal through the forward and rearward outlet holes and withdrawing the vaginal douche applicator from the vaginal canal.

52. A method of vaginal douching as recited in claim 42 wherein said step of introducing includes introducing a vaginal douche applicator having a stainless steel external surface, said step of supplying includes supplying water to the internal passage and further including the step of neutralizing vaginal odors due to contact of vaginal tissue with the stainless steel external surface in the presence of the water.

* * * * *